United States Patent [19]
Rothman

[11] Patent Number: 4,514,504
[45] Date of Patent: Apr. 30, 1985

[54] MONITORING METHOD FOR POLYACRYLIC ACIDS IN AQUEOUS SYSTEMS

[75] Inventor: Alan M. Rothman, Jenkintown, Pa.

[73] Assignee: Rohm and Haas Company, Philadelphia, Pa.

[21] Appl. No.: 516,613

[22] Filed: Jul. 22, 1983

[51] Int. Cl.$^3$ .................. G01N 1/00; G01N 31/06; B01D 15/00; B01D 12/00
[52] U.S. Cl. ........................... 436/85; 436/104; 436/129; 436/175; 436/178; 210/668; 210/670; 210/691
[58] Field of Search .................. 436/79, 85, 104, 129, 436/161, 178, 175; 422/70; 210/635, 668, 669, 691, 670

[56] References Cited

U.S. PATENT DOCUMENTS

| | | | |
|---|---|---|---|
| 3,531,463 | 9/1970 | Gustafson | 210/674 |
| 3,920,398 | 11/1975 | Small et al. | 436/129 |
| 4,314,823 | 2/1982 | Rich, Jr. et al. | 422/70 |

FOREIGN PATENT DOCUMENTS 1560996  2/1980  United Kingdom ............... 210/669

OTHER PUBLICATIONS

Kunin, Robert; "Porous Polymers as Adsorbents-A Review of Current Practice;" *Amber-Hi-Lites*, No. 163; Rohm and Haas Co.; 1980.

*Primary Examiner*—Arnold Turk
*Assistant Examiner*—Carol M. Delahunty
*Attorney, Agent, or Firm*—Marc S. Adler

[57] ABSTRACT

A quantitative method useful for field monitoring low concentrations of water soluble, polyacrylic acids in aqueous systems containing polyacrylic acids and other soluble ionic materials, such as ionic salts and phosphonates, is provided. The method involves adjusting the pH of the aqueous system to suppress the ionization of the polyacrylic acids followed by selective adsorption and concentration of the polyacrylic acids on a suitable adsorbent. Concentrated polyacrylic acids are then desorbed from the adsorbent and the concentration of the polyacrylic acids in the aqueous system is determined by conventional techniques.

12 Claims, No Drawings

MONITORING METHOD FOR POLYACRYLIC ACIDS IN AQUEOUS SYSTEMS

BACKGROUND OF THE INVENTION

This invention relates to a simple, quantitative method for isolating and concentrating water soluble, polyacrylic acids from dilute aqueous systems containing polyacrylic acids and the other soluble ionic materials. More particularly, the invention relates to a method for selectively adsorbing and concentrating low concentrations of ionization suppressed polyacrylic acid, polymethacrylic acid, mixtures and copolymers thereof (hereinafter defined as polyacrylic acids) from aqueous systems containing these polyelectrolytes and other soluble ionic materials, such as ionic salts and phosphonates. These soluble ionic materials typically interfere with the ability of conventional techniques to monitor the concentration of the polyacrylic acids in aqueous systems.

Water soluble polyacrylic acid, polymethacrylic acid, polymaleic acid, and copolymers formed from at least 50 weight percent of acrylic, methacrylic, or maleic acid and less than 50 weight percent of another copolymerizable monomer and mixtures thereof, referred to hereinafter generally as polyacrylic acids, are used commercially as scale inhibitors and dispersants in such aqueous systems as cooling towers, boilers, oil field production facilities, sea water evaporators, and detergents. These polymers interact with scale forming, inorganic salts formed by the reaction of hardness ions, such a calcium and magnesium, with anions such as carbonate, phosphate and sulfate. The polyacrylic acids function by interfering with the growth of the crystals of these salts (antiprecipitation), or by introducing a repulsive surface charge to the crystals retarding their agglomerating, settling and depositing on surfaces (dispersion), or by interfering with the structure of the crystal itself making the scale more easily fracturable and dispersable (crystal modification). In addition, these polymers are also useful for dispersing other suspended particulate matter, such as clay, in aqueous systems. Rohm and Haas Company's ACRYSOL® LMW polymers of polyacrylic acids and their corresponding sodium salts, having weight average molecular weights ranging from about 1,000 to about 4,500, are known to be effective scale inhibitors in aqueous system to inhibit common hardness ion salts. In addition, U.S. patent application Ser. No. 485,560 also relates to water soluble, low molecular weight copolymers of acrylic acid and methacrylic acid which are useful for scale inhibition in aqueous systems. Further, U.S. patent application Ser. No. 485,559 relates to a method of dispersing inorganic materials in aqueous systems using low molecular weight copolymers of acrylic acid and hydrophobic comonomers.

Other organic compounds, such as organophosphates and organophosphonates, are also commonly used as scale inhibitors in aqueous systems. One such group of organic phosphonate scale inhibitors are manufactured and sold by Monsanto Chemical Company under the trademark Dequest®. In addition, other ionic compounds, such as inorganic phosphates, may also be used in these aqueous systems to assist in retarding the corrosion of metal surfaces.

Presently there is no simple, fast, reproducible, and sensitive, low cost method for selectively determining the concentration of polyacrylic acids in aqueous systems containing other soluble ionic materials such as hardness ions and phosphonates. The presence of these soluble ionic materials in the aqueous system interferes with the ability of conventional methods to measure small concentrations of polyacrylic acids, on the order of about 5 ppm or less, in such aqueous systems. One such technique in which soluble ionic salts interfere with the determination of the concentration of polyacrylic acids involves precipitation with bivalent copper, filtration, redissolution of the precipitate, and assay of unreacted bivalent copper (U.S. Pat. No. 3,516,795).

A suitable method for determining the concentration of polyacrylic acids in aqueous systems containing soluble ionic materials must be fast, simple, and capable of yielding reproducible results. It must avoid the use of toxic or hazardous chemicals, must be able to completely isolate polyacrylic acids from organic phosphonates, must be able to concentrate polyacrylic acids from the aqueous system to gain sensitivity, and must be capable of eliminating possible interference in the measurement caused by corrosion inhibitors, inorganic salts, colored impurities, and interspersed oil droplets.

Such a simple, fast, reproducible, and sensitive, low cost method for determining the concentration of polyacrylic acids in aqueous systems containing other soluble ionic materials is desired by operators of cooling towers, boilers, and other systems which use polyacrylic acids as scale inhibitors or dispersants. Such a monitoring method would allow operators to make economical decisions in the field concerning the timing and need for additional polyacrylic acids.

It is therefore an object of the present invention to provide a solution to the problem of monitoring the concentration of polyacrylic acids in aqueous systems by providing a simple, fast, reproducible, and sensitive, low cost method for selectively adsorbing and concentrating polyacrylic acids from aqueous systems containing other soluble ionic materials so that the concentration of the polyacrylic acids in the aqueous system can be determined.

It is also an object of the present invention to provide a method for quantitatively monitoring the concentration of polyacrylic acids in aqueous systems containing polyacrylic acids and other soluble ionic materials.

It is a further object of the invention to provide a method for determining the concentration of both polyacrylic acids and organic phosphonates in aqueous systems containing such compounds.

SUMMARY OF THE INVENTION

I have found that the above objectives can be realized by a novel method for selectively adsorbing and concentrating low levels of water soluble, polyacrylic acids from aqueous systems containing polyacrylic acids and other soluble ionic materials by suppressing the formation of polyacrylic acid ions followed by selectively adsorbing the ionization suppressed polyacrylic acids using an effective adsorbent medium, and desorbing the concentrated, adsorbed polyacrylic acids, free of interfering ionic impurities, for subsequent quantitative determination.

This method is fast, simple, reproducible, safe accurate, low in cost, and especially useful at a field location for routine monitoring operations.

DETAILED DESCRIPTION OF THE INVENTION

The method of this invention is directed to the quantitative determination of low levels of water soluble, polyacrylic acid, polymethacrylic acid, polymaleic acid, and copolymers formed from at least 50 weight percent of acrylic, methacrylic or maleic acid and less than 50 weight percent of other copolymrizable comonomers and mixtures thereof. Suitable comonomers include acrylamide, lower alkyl acrylates, lower alkyl methacrylates, hydroxy alkyl acrylates, and hydroxy alkyl methacrylates where the alkyl group contains from 1 to about 4 carbon atoms, and the like. These copolymers, in their acid form, are soluble in aqueous systems containing such polymers and other soluble ionic materials. The polyacrylic acids may have a weight average molecular weight ranging from about 1,000 to about 60,000. Higher molecular weight polyacrylic acids are also suitable in this invention as long as they are water soluble. The polyacrylic acids may be prepared using any conventional synthesis route including, but not limited to, the methods described in U.S. Pat. Nos. 4,314,004; 4,301,266; and 3,646,099 for preparing low molecular weight polyacrylic acids. Accordingly, the polymer chain of the polyacrylic acids may be terminated with any suitable chain terminating moiety, such as isopropanol, 3-mercaptopropionic acid, sodium bisulfite, and the like, without affecting the method of the present invention.

The method of this invention requires three basic steps: (1) the suppression of ions of the polyacrylic acids in the aqueous system; (2) adsorption and concentration of the ionization suppressed polyacrylic acids onto an effective adsorbent; and (3) desorption of the adsorbed polyacrylic acids from the adsorbent utilizing a small volume of an effective displacement medium which is compatible with subsequent conventional assay methods for quantitatively measuring the concentration of the polyacrylic acids.

Prior to the ionization suppression step, it may be desirable to filter a sample of the aqueous solution containing the polyacrylic acids and other soluble ionic materials. This filtration step is useful for removing particulates and/or suspended oil droplets which may be present in the sample and, which if not removed, would contaminate the adsorbent reducing its effectiveness and ability to be re-used. Any filter media which is compatible with the aqueous system sample can be used to remove the particulate material. I have found that filters having a pore size of about 5.0 micrometers in diameter are preferred for this application. Filters having much smaller pore diameters have been found to clog too rapidly and may not, therefore, be capable of handling a sufficient sample volume. The most preferred filter has been found to be a Gelman Associates, Acrodisc ® 5.0 micrometer, disposable filter assembly attached to a syringe fitted with a plunger. This filter assembly has been found to be very convenient to handle and the syringe attachment allows for rapid filtration of the sample.

If oil droplets are dispersed in the sample, they may be removed by first passing the sample through standard filter paper, such as 12.5 cm Whatman No. 41 ashless, folded in a cone, and supported in a funnel. More preferably, I have found that glass wool packed into the bottom portion of the syringe above the attached Acrodisc ® filter is excellent for complete removal of oil droplets from the sample.

After the particulates and/or oil droplets have been removed from the sample, the polyacrylic acids in the sample are ionization suppressed. This ionization suppression step is critical in preparing the polyacrylic acids for subsequent selective adsorption and concentration. Polyacrylic acids are ionization suppressed by the addition of a suitable quantity of an acid such as hydrochloric, nitric, or sulfuric acid. While nitric acid has been found to be the most preferred acid, sulfuric acid may be preferred in certain instances due to safety considerations. Polyacrylic acids are sufficiently ionization suppressed when the pH of the sample has been reduced to less than about 3.5. At pH of about 1 or lower, however, other ions in the sample, such as the organic phosphonates, will also become neutralized. Further, at below about pH 2 the cartridge may begin to degrade. The neutralization of the other soluble ions in the sample is not desired since, if they were so neutralized, the adsorption step would not be selective for the adsorption of polyacrylic acids. Therefore, the pH of the sample should be adjusted to from about 3.0 to about 2.0 and preferably to about 2.5. If the pH of the sample is unintentionally lowered below about 2, then back correction of the pH may be made by the addition of a suitable amount of a base such as sodium hydroxide. The pH adjustment may be accomplished by standard titration and the pH tested by pH indicator paper, by the use of a standard pH meter, or other suitable techniques. After the polyacrylic acids in the sample have been ionization suppressed by pH adjustment, the sample is ready for selective adsorption.

Selective adsorption and concentration of the ionization suppressed, polyacrylic acids is accomplished by passing a suitable volume of the sample through a non-polar, adsorbent. The adsorbent must have the capability and capacity to selectively and completely adsorb, and thereby concentrate, small concentrations of ionization suppressed polyacrylic acids while allowing the adsorbed materials to be easily desorbed therefrom by the use of a small quantity of a non-interfering, displacement fluid. The adsorbents which have been found to be suitable for the method of this invention include nonpolar, bonded phase, silica gels, and certain organic polymeric resins. The silica gel type adsorbents include octadecylsilane bonded to silica gel such as Sep-Pak ® C-18, manufactured by Waters Associates, Baker-10 octadecyl, manufactured by J. T. Baker Company and Bond Elut ® $C_{18}$ ® manufactured by Analytichem International. Silica gel coated with octylsilane is also a suitable adsorbent for the process of the invention. The organic polymeric resins which can also be used in this invention include rigid, macroreticular styrene-divinylbenzene copolymer resins having adsorptive properties similar to the above packings, such as PRP-1 ® manufactured by Hamilton Company. The preferred adsorbent for use in the invention is the Sep-Pak ® $C_{18}$ cartridge. The adsorbents may be packed into a column but are preferably used in the form of small cartridges fitted with a syringe.

Prior to passing the ionization suppressed, polyacrylic acid sample through the adsorbent, it is desirable to condition the adsorbent as by properly wetting the adsorbent. This conditioning may be conducted by treating the adsorbent with methanol followed by a water rinse, the water being at about the same pH as the ionization suppressed, polyacrylic acid sample.

The ionization suppressed polyacrylic acid sample is then passed through the adsorbent. The best technique for conducting the adsorption is by attaching the top of the adsorbent cartridge to the fitting of a three-way syringe valve connected to a 50 cc Luer-Lock syringe. The sample is then fed downflow through the syringe, through the valve and through the adsorbent cartridge.

The top of the syringe may be fitted with a plunger to force the sample through the adsorbent at a rapid rate of about 25 milliliters per minute. Subatmospheric pressure (vacuum) can also be applied to the syringe to force the sample through the adsorbent. The water, hardness ions, phosphates, and phosphonates are not adsorbed and exit the adsorbent as effluent. This effluent may be collected, as it leaves the adsorbent, for subsequent phosphonate analysis.

The adsorbed, ionization suppressed, polyacrylic acids are therefore selectively concentrated on the adsorbent. The volume of the sample passed through the adsorbent is recorded so that the concentration of the polyacrylic acids in the aqueous system sample can be determined. By increasing the volume of the sample fed to the adsorbent, the sensitivity of the concentration measurement of the polyacrylic acids in the sample will be increased.

The adsorbed, ionization suppressed, polyacrylic acids are then desorbed from the adsorbent by the use of a suitable displacement fluid which completely displaces adsorbed polyacrylic acids and does not interfere with the ability of the adsorbent to be reused. A suitable displacement fluid is an aqueous solution of 0.1 normal sodium hydroxide. When the displacement fluid is to be added to the syringe, the valve should be closed to the cartridge and the plunger removed. When the valve is not attached, the adsorbent cartridge should first be removed to prevent disturbance of the adsorbent. The three-way Luer-Lock valve, which is preferably used in the practice of this invention, allows for variety of operations. One position of the valve is closed to the cartridge and the air. When the valve effluent pathway is positioned in the direction of liquid flow through the syringe, the liquid passes directly through the cartridge. This position is used during conditioning, adsorption, and desorption. When the valve effluent pathway is positioned in a direction perpendicular to flow through the syringe, the syringe effluent pathway is to air. This position allows for the removal of the syringe plunger without disturbing or removing the cartridge. This valve position also allows for drawing a reagent up into the syringe for subsequent passage through the cartridge without removal of the plunger. When the three-way valve is not connected to the syringe, the cartridge must be removed before the syringe plunger is pulled back to allow for the addition of additional fluid. After the plunger is removed, the cartridge may then be replaced and the displacement fluid is pushed through the adsorbent with the reinserted plunger.

Methanol, sodium hydroxide solution, or other suitable displacement fluids may be used to desorb the adsorbed polyacrylic acids. Desorbing the polyacrylic acids using methanol is preferred since the adsorbent is also being conditioned for subsequent adsorption. If a sodium hydroxide solution is used as the displacement fluid, the adsorbent should be re-conditioned prior to subsequent adsorption.

The desorbed polyacrylic acid solution is collected for subsequent assay. A number of conventional methods are available to measure the concentration of polyacrylic acids in a concentrated solution of the displacement fluid in the absence of other soluble ionic materials. The concentration of the polyacrylic acids in the aqueous system may then be calculated based on the concentration of the desorbed polyacrylic acids in the known volume of displacement fluid and the initial volume of the aqueous system sample.

The following are some of the conventional assay methods which can be used to measure the concentration of the desorbed polyacrylic acids in the displacement fluid.

One method is based on the formation of an insoluble complex between polyacrylic acids and a cationic surfactant, followed by the determination of resulting turbidity by absorbance measurements and a calculation of the concentration from a calibration curve. The cationic surfactant is preferably a 0.06 percent solution of diisobutylphenoxyethoxyethyl dimethyl benzyl ammonium chloride monohydrate, such as Hyamine 1622 ® manufactured by Rohm and Haas Company, in deionized water. A citrate buffer of 3% solution of trisodium citrate dihydrate in deionized water is first pipetted into the polyacrylic acid solution followed by the cationic surfactant solution. The solutions are allowed to stand undisturbed for about 30 minutes and the absorbance is measured with a spectrophotometer at 800 nanometers. The absorbance of a polyacrylic acid solution without complexing agents is used as a control. The concentration of the polyacrylic acids in the sample is then calculated using a calibration curve.

Another method for determining the concentration of polyacrylic acids in water, in the absence of other soluble ionic impurities, is a colorimetric technique utilizing calcium carbonate and a solution of methylene blue. The polyacrylic acid solution is passed through a column of analytical grade calcium carbonate. The adsorption column containing the calcium carbonate can be a funnel fitted with a medium porosity fritted disk, such as Corning Inc. Number 36060. After the polyacrylic acid solution is adsorbed onto the calcium carbonate column, a solution of methylene blue, in distilled or deionized water, is passed through the column. The amount of methylene blue adsorbed by the polyacrylic acids is determined by eluting the column with water and measuring the optical absorbance at 660 nanometers, as compared to standard solutions and blanks, using a suitable spectrophotometer or filter photometer with a red filter.

Another method for determining the concentration of polyacrylic acids in aqueous solutions utilizes an aqueous solution of mercurous acetate buffered with one normal acetic acid and the use of a blue dye, such as 1% diphenyl carbazone. The polyacrylic acid solution containing a specified amount of the mercurous acetate buffer solution is heated to 85° C. for 20 minutes to form a precipitate. The precipitate is filtered immediately with a suitable filter paper. The precipitate is washed with water to remove soluble materials. The blue dye is then added to the filter paper, washed with about 50 ml water, and the color of the filter paper is visually compared to standard colored papers. The dye is also added to the filtrate to determine if any polyacrylic acids were not precipitated.

A still further method for measuring the concentration of the desorbed polyacrylic acids is an iron-thiocyanate colorimetric method described in *Chemistry and Technological Waters*, U. Glukhova, P. A. Perov, Kiev (Russia), 3(3), p 236–237 (1981). This method is based on the formation of a colorless complex between iron (III) and polyacrylic acids while a complex formed between iron (III) and thiocyanate ions is red. Therefore, a decrease in the color of iron-thiocyanate complex, upon complexing of iron with polyacrylic acids, is directly proportional to the polyacrylic acid concentration. The reaction involved between iron III ($Fe^{+3}$) and polyacrylic acids (PAA) is as follows:

$$xFe^{+3} + y(PAA) \rightarrow Fe_x(PAA)_y$$

After the iron (III) has been allowed to complex with the polyacrylic acids to form the colorless $Fe_x(PAA)_y$ complex, potassium thiocyanate is added as an aqueous solution to the $Fe_x(PAA)_y$ complex. The thiocyanate ($SCN^-$) ions will react with non-complexed iron (III) ions to form the red iron-thiocyanate complex according to the reaction:

$$Fe^{+3} + nSCN^- \rightarrow Fe(SCN)_n^{(3-n)}$$

where n=1, 2 or 3. Therefore, the color of the resulting solution can be correlated with the quantity of iron (III) and thiocyanate ion added to arrive at the concentration of the polyacrylic acids. The color of the resulting solution, in terms of the percentage of light transmitted therethrough, is an accurate measure of the polyacrylic acid concentration. This assay method is especially suitable for use with the method of the invention because it is fast, sensitive, and because sulfate ions, introduced during ion suppression when using sulfuric acid, do not interfere with the procedure. The sensitivity of the method is a function of the molecular weight of the polyacrylic acids and increases with increasing polyacrylic acid molecular weight. Therefore, the molecular weight of the polyacrylic acids that have previously been added to the aqueous system should be recorded prior to relying on the accuracy of the results of this method for polyacrylic acids having other molecular weights.

The method of the present invention is also useful for simultaneously measuring the concentration of organic phosphonates in aqueous systems. The phosphonates, which are not adsorbed with the polyacrylic acids, may be collected and assayed using conventional techniques. One such assay method utilizes thorium (IV) nitrate to form a stable colorless complex with organic phosphonates. After the organic phosphonates are complexed, xylenol orange may be used as an indicator. The xylenol orange complexes with the noncomplexed thorium (IV) forming a bright pink color. This complex-colorimetric titration is specific for organophosphonates. Polyacrylic acids and/or other soluble ionic materials do not interfere with the technique.

The following examples are intended to illustrate, and not to limit, the invention.

EXAMPLES 1-6

"Five or ten parts per million of radiotagged $C_{14}$ Acrysol ® LMW-20X polyacrylic acid and 10 parts per million of Dequest ® 2010 organic phosphonate were added to each of six samples of oil well production water." The source of the water and the concentration of the polyacrylic acid is illustrated in Table I.

Sixty milliliters of each of the samples were separately passed through a 50 milliliter disposable syringe. In the case of a sample contaning oil droplets, Sample 6, the syringe was packed with 15 milliliters of glass wool. All the syringes were fitted with a Gelman Associates Acrodisc ® 5.0 micrometer disposable filter assembly. The flow rate of the sample through the syringe was about 50 mL/min. The filtered aqueous samples were then pH adjusted to about pH 2.5 to suppress polyacrylic acid ion formation with 2N nitric acid.

An adsorbent cartridge of Sep-Pak ® $C_{18}$ was conditioned for use by attaching it to a three-way syringe valve mounted on a 50 cc. Luer-Lock syringe. About 10 milliliters of methanol was passed through the cartridge at a rate of about 25 mL/min followed by about 25 milliliters of water, adjusted to a pH of about 2.5, at a flow rate of about 25 mL/min. 50 mL each of the ionization suppressed, filtered polyacrylic acid containing samples was separately passed through a conditioned adsorbent cartridge. The plunger at the top of the syringe provided for a flow rate of the sample through the cartridge of about 25 mL/min. The non-absorbed effluent was collected in a beaker. Following the adsorption and concentration step, the polyacrylic acid was desorbed from the cartridge by the use of 10 mL of 0.1 normal sodium hydroxide displacement fluid at a rate of about 10 mL/min. The desorbed and concentrated (five times) polyacrylic acid was collected in a beaker.

The collected polyacrylic acid effluent was pH adjusted to 2.5 with nitric acid. One half milliliter of ferric chloride solution, prepared from 1.00 gram $FeCl_3.6H_2O$ plus 2.5 ml concentrated nitric acid in 1 liter deionized water, was added to the pH adjusted polyacrylic acid effluent. The sample was allowed to sit for 5 minutes. Following this time, one milliliter of potassium thiocyanate solution, prepared from 9.6 grams KSCN in 50 mL deionized water, was added followed by the addition of 8.5 mL of pH 2.5 water. About 10 mL of this complexed solution containing the polyacrylic acid, iron chloride and potassium thiocyanate is removed and the intensity of the color was measured using a Hach colorimeter (model DR 100) and compared against a calibrated color standard of polyacrylic acid. The concentration of the polyacrylic acid in the initial sample was then calculated based on the volume of the sample and the dilutions. This procedure was followed for all samples.

In addition, the effluent from the adsorption and concentration step was also assayed using the thorium nitrate/xylenol orange method for the concentration of organic phosphonate in the aqueous sample. The results of these assays are presented in Table I and compared with a $C_{14}$ scintillation analysis conducted on the desorbed polyacrylic acid solution.

TABLE I[2]

| | | Concentration of Acrysol LMW 20X ® $C_{14}$ Radiotagged) | Polyacrylic Acid Concentration Measurement | | Thorium Nitrate |
|---|---|---|---|---|---|
| Sample | Water Type | ppm 1,4 | $C_{14}$ Count ppm | Fe/SCN Test ppm | Organic Phosphonate ppm |
| 1 | South Delta Offshore La. | 5 | 4.4 | 3.2 | 10 |

TABLE I[2]-continued

| Sample | Water Type | Concentration of Acrysol LMW 20X ® C[14] Radiotagged) ppm 1,4 | Polyacrylic Acid Concentration Measurement | | Thorium Nitrate Organic Phosphonate ppm |
|---|---|---|---|---|---|
| | | | C[14] Count ppm | Fe/SCN Test ppm | |
| 2 | Marathon Oil Co., Tensleep Field, Oregon Basin, Cody, WY | 5 | 4.2 | 4.2 | 10 |
| 3 | Conroe Field E. Texas | 10 | 7.7 | 8.2 | 10 |
| 4 | Duncan, OK | 10 | 7.8 | 8.4 | 10 |
| 5 | Texaco W. Texas | 5 | 4.0 | 4.2 | 10 |
| 6 | Long Beach, CA | 5 | 3.9 | 4.2 | (3) |
| | | 10 | 9.2 | 8.2 | |
| | | 10 | 8.2 | 10.0 | |
| 7 | Tap Water | 7 | 6.0 | 8.0 | 10 |
| | | 3.5 | 3.1 | 3.4 | 10 |

[1]Acrysol LMW-20X is a polyacrylic acid having a weight average molecular weight of about 2000.
[2]All samples were charged with 10 ppm Dequest ® 2010 organic phosphonate. This compound has the structural formula:

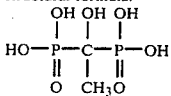

[3]Could not be detected due to yellow color of sample.
[4]C[14] radiotagged samples found to contain 12% radioimpurity The test shows that the concentration of polyacrylic acids in the sample was determined within +20% accuracy using a five-fold concentration. At a five-fold concentration, a concentration as low as about 1 ppm can be detected when a five-fold concentration is used. Accordingly, the method of the invention is sufficiently accurate for the determination of the concentration of polyacrylic acids in aqueous systems containing other soluble ionic materials for use as a monitoring method at a field location. If the sample and adsorbent volumes are increased and more polyacrylic acids are adsorbed and concentrated on the adsorbent, the sensitivity of the method increases. Further, since the volume of the sample and the adsorption system can be increased in scale, the concentration of very small concentrations of polyacrylic acids on the order of as low as 0.1 ppm can be determined.

EXAMPLE 7

This example demonstrates that other soluble ionic compounds in aqueous systems do not interfere with the adsorption/concentration method of this invention. Ten parts per million of zinc sulfate was added to Sample 7 of example 1 containing 10 ppm of radiotagged Acrysol ® LMW-20X. The procedure of example 1 was repeated and the concentration of the Acrysol LMW-20X was determined by the method of the invention. The radiotagged scintillation method used for comparison purposes measured 7.0 ppm polyacrylic acids in the sample prior to adsorption. The method of the invention determined the presence of 7.6 ppm polyacrylic acids in the sample. Accordingly, the concentration of polyacrylic acids measured according to the method of the invention is not disturbed by the presence of other soluble ionic impurities such as zinc or sulfate ions.

EXAMPLE 8

This example was similar to example 7 except that 25 ppm sodium lignosulfonate, dispersant, was added to Sample 7 containing 5 ppm radiotagged Acrysol ® LMW-20X. The polyacrylic acid count (via scintillation) prior to the test was 4.1 ppm. The concentration of polyacrylic acids determined by the procedure of example 1 was 5 ppm. Therefore, the presence of dispersants, such as sodium lignosulfonate, in aqueous systems does not interfere with the polyacrylic acid concentration determination.

EXAMPLE 9

Acrylic Acid/Ethyl Acrylate Copolymer

A radiotagged sample of a low molecular weight (about 3000 weight average molecular weight) copolymer formed from about 95 weight percent acrylic acid and about 5 weight percent ethyl acrylate with the addition of 10 ppm Dequest 2010 was prepared and tested using the same procedure as described for Examples 1–6. The sample contained 8.1 ppm of the copolymer. It was concentrated five-fold and desorbed using sodium hydroxide. The colorimeter measured as concentration of 37.8 ppm versus the actual concentration of 40.5 ppm indicating that the method is sensitive for measuring the concentration of acrylic acid copolymers in aqueous systems.

EXAMPLES 10–17

Screening Tests

The following examples were performed to determine the utility of the method of the invention, as described in Examples 1–6, for measuring the concentration of other polyacrylic acids. Radiotagged samples of all the following polyacrylic acids were not available and, accordingly, a before and after adsorption/colorimetric test method (iron-thiocyanate) was utilized. An aqueous sample containing a known concentration (10 ppm unless otherwise indicated) of a polyacrylic acid to be measured was prepared, ionization suppressed by adjusting the pH to pH 2.5, concentrated five times using a C[18] packing, and desorbed with sodium hydroxide. A control sample of sodium hydroxide containing the polyacrylic acid, at the same concentration as would be achieved upon 100 percent adsorption and desorption of the sample to be tested after a five fold concentration, was also prepared. Both samples were subjected to an iron-thiocyanate colorimetric test and the percent transmittance of each was recorded and compared. Differences in the percent transmittance achieved between the adsorbed sample and the control was due to breakthrough and/or incomplete desorption.

Examples 10 and 11 evaluated whether the method was applicable for other commercial, low molecular weight polyacrylic acid homopolymers. Example 10 utilized Goodrite K-752 ® polyacrylic acid, chain terminated using isopropanol, and Example 11 was of (20 ppm) Colloid 211 ® polyacrylic acid, chain terminated with 3-mercaptopropionic acid. Example 10 resulted in a 40% transmittance while the control yielded 32% transmittance indicating the utility of the method and good agreement using the screening test despite some breakthrough or incomplete desorption. Example 11 showed a 30% transmittance while the control averaged 32% transmittance, also evidencing good agreement.

Example 12 evaluated a higher molecular weight polyacrylic acid, Rohm and Haas Company's Acrysol ® A-1, having a weight average molecular weight of about 60,000. The sample recorded a 28% transmittance while the control read 40% transmittance, indicating that the test method was applicable despite a greater degree of breakthrough.

Example 13 was of a polymethacrylic acid product, ($M\bar{w}$ about 5000), Rohm and Haas Company Tamol 960 ®. Instead of a 10 ppm concentration, the sample contained 120 ppm and was concentrated five times. The control contained 600 ppm. The samle resulted in a 52% transmittance in very close agreement with the control (56%) transmittance.

Example 14 was of a polyacrylic acid copolymer, formed from about 70 percent acrylic acid and about 30 percent methacrylic acid, having the weight average molecular weight of about 3400. 100 percent agreement (36% transmittance) between the sample (10 ppm with five fold concentration) and the control was found.

Example 15 was of another polyacrylic acid copolymer, formed from about 65 percent acrylic acid and about 35 percent hydroxypropyl acrylate, having a weight average molecular weight of about 3000. The percent transmittances of the sample (30%) and the control (34%) were in close agreement.

Example 16 was of another polyacrylic acid copolymer formed from about 92 percent acrylic acid and about 8 percent acrylamide having a weight average molecular weight of about 2300. Using a 10 ppm concentration sample with five fold concentration the percent transmittance of the sample was 44% and the control 42%.

The samples of Examples 15 and 16 were prepared with 10 ppm of the Dequest 2010. The Dequest 2010 was collected as adsorption effluent and the concentration of the phosphonate was tested using the thorium nitrate test described in Examples 1-6. Full accountability (10 ppm) of the phosphonate was found, indicating that the method of the invention is applicable for isolating and measuring the concentration of soluble ionic impurities in aqueous systems, as well as separating and measuring the concentration of polyacrylic acids.

Example 17 was of a polymaleic acid having a weight average molecular weight of about 1000 and a solids content of 50.8 percent by weight manufactured by Ciba-Geigy Corporation under the trademark Belgard ®. A sample containing 200 ppm polymaleic acid and 20 ppm Dequest ®2010 and a control sample containing 1000 ppm of the polymaleic acid were prepared and evaluated using the screening test method. The adsorbed sample resulted in a 49% transmittance and the control measured 46% transmittance.

The results of the screening tests (Examples 10-17) establish that the method of the invention is applicable to polyacrylic acid homopolymers of a wide molecular weight range, polymethacrylic acid homopolymers, polymaleic acid polymers, polyacrylic/methacrylic acid copolymers, polyacrylic/lower alkyl acrylate copolymers, polyacrylic/acrylamide copolymers, and polyacrylic/hydroxy alkyl acrylate copolymers. Accordingly, as long as polyacrylic acid is present in the polymer, copolymer, or a mixture thereof, at a concentration of about 50 weight percent or more, the method of this invention is useful for adsorbing, concentrating, and separating the polyacrylic acids from an aqueous solution for subsequent determination of the concentration of the polyacrylic acids in the sample. Losses of polyacrylic acids on the adsorbent or breakthrough resulting from the method can be corrected by calibrating the test results by first running a screening test as described in these examples with controls containing known concentrations of the polyacrylic acids.

ANTIPRECIPITATION TEST

Example 18 illustrates that the method of the invention is useful for measuring the concentration of polyacrylic acid in aqueous systems containing polyacrylic acid and common hardness ions. Polyacrylic acids in effluent water, such as oil well production effluent, may possess little residual antiprecipitation activity after the polyacrylic acids have interacted with inorganic salts and clay present in the aqueous system. A two-stage, laboratory, antiprecipitation test was conducted to simulate field conditions and to demonstrate the utility of the method of the invention under such conditions. Acrysol LMW-20X polyacrylic acid was exposed to a supersaturated calcium carbonate solution. The antiprecipitation activity of the polyacrylic acid was measured and the concentration of the polyacrylic acid, which had not interacted with the hardness ions, was measured using the method of the invention as described in the previous screening tests.

Two stock solutions A and B were prepared.

| Stock Solution A | Stock Solution B |
|---|---|
| 2.10 g/L $CaCl_2$ | 0.85 g/L $Na_2CO_3$ |
| 2.04 g/L KCl | 2.04 g/L KCl |
| 4.97 g/L $MgCl_2.6H_2O$ | 4.97 g/L $MgCl_2.6H_2O$ |
| 76.68 g/L NaCl | 76.68 g/L NaCl |

To an eight ounce jar was added 100 mL of Stock Solution A followed by the addition of 0, 6 or 10 mL of pH 8, 0.1 weight percent Acrysol LMW-20X solution to form an initial polyacrylic acid concentration of 0, 30 ppm and 50 ppm, respectively. One hundred milliliters of Stock Solution B was then added to each jar. Each jar was then sealed and placed in a 70° C. shaking water bath for 16 hours. Each sample was then removed from the water bath, cooled for one hour, and filtered through a 0.45 micrometer Millipore filter to remove precipitate and associated polyacrylic acid. A portion of each filtrate was then analyzed for residual calcium ions by a standard EDTA titration technique and for residual polyacrylic acid concentration using the method of the invention. This was accomplished by first establishing a calibration curve of the percent transmittance versus the concentration of the polyacrylic acid using control samples of known polyacrylic acid concentration. The actual concentration of the polyacrylic acid in the filtrate was then determined by measuring the percent transmittance of the polyacrylic acid in the filtrate as obtained by the method of the invention, as described in the screening test examples, followed by utilizing the calibration curve.

The percent antiprecipitation or antiprecipitation activity was calculated as follows:

$$\% \text{ antiprecipitation} = \frac{[Ca^{++}] \text{ residual}}{[Ca^{++}] \text{ initial}} \times 100$$

The second step of the test involved adding 1 mL of 10.5 g/L $Na_2CO_3$ to 100 mL of each of the remaining, unanalyzed filtrates of the first step. The jars were then sealed, shaken in a 70° C. water bath for 16 hours, removed from the bath, cooled for one hour, filtered through 0.45 micrometer Millipore filter and analyzed as described above for percent antiprecipitation and residual polyacrylic acid ion concentration.

The results of these two step, antiprecipitation tests are presented in Table II. The results clearly demonstrate that the method of the invention provides a useful correlation between the concentration of residual polyacrylic acid in an aqueous system and the antiprecipitation activity achieved as a function of the initial concentration of polyacrylic acid added to the aqueous sample.

TABLE II
ANTIPRECIPITATION TEST

| Initial Polyacrylic Acid Concentration (ppm) | Antiprecipitation Percent | Residual Polyacrylic Acid Concentration (ppm) |
|---|---|---|
| After First Precipitation | | |
| 0 | 60 | — |
| 30 | 95 | 8.4 |
| 50 | 97 | 14.0 |
| After Second Precipitation | | |
| 0 | 55 | — |
| 30 | 75 | 4.0 |
| 50 | 98 | 8.5 |

What is claimed is:

1. A method for concentrating and separating polyacrylic acids from an aqueous system containing polyacrylic acids and other soluble, ionic materials comprising:
    (a) adjusting the pH of said aqueous system to suppress ionization of said polyacrylic acids;
    (b) selectively adsorbing said ionization suppressed, polyacrylic acids on a nonpolar adsorbent and separating said other soluble ionic materials and aqueous solution from said adsorbed, ionization suppressed polyacrylic acids; and
    (c) desorbing said adsorbed, ionization suppressed polyacrylic acids from about adsorbent with a suitable volume of a displacement fluid.

2. The method of claim 1 where said polyacrylic acids are water soluble polymers selected from the group consisting of homopolymers of polyacrylic acid, polymethacrylic acid, and polymaleic acid copolymers formed from at least 50 weight percent acrylic acid, methacrylic acid, or maleic acid and less than 50 weight percent of a different copolymerizable monomer, and mixtures of said homopolymers and copolymers.

3. The method of claim 1 where said other soluble, ionic materials comprise organophosphonates and hardness ion salts.

4. The method of claim 1 where the pH of said aqueous system is adjusted to a pH ranging from about pH 2 to about pH 3.5 to suppress ionization of said polyacrylic acids.

5. The method of claim 1 where said adsorbent comprises octadecyl silane bonded to silica gel.

6. The method of claim 1 where said adsorbent comprises a rigid, macroreticular styrene-divinylbenzene copolymer.

7. The method of claim 1 where said displacement fluid is an aqueous solution capable of completely displacing the adsorbed polyacrylic acids without interfering with the capability of the adsorbent to be reused.

8. A method for quantitatively determining the concentration of polyacrylic acids and organophosphonates in an aqueous system comprising:
    (a) adjusting the pH of said aqueous system to suppress ionization of said polyacrylic acids;
    (b) selectively adsorbing said ion suppressed polyacrylic acids on a non-polar adsorbent and separating said organophosphonates and aqueous solution from said adsorbed, ion suppressed polyacrylic acids;
    (c) collecting the non-adsorbed aqueous system containing said organophosphonates;
    (d) desorbing said adsorbed, ionization suppressed, polyacrylic acids from said adsorbent with a suitable displacement fluid;
and subsequently measuring the concentration of the desorbed polyacrylic acids and the non-adsorbed organophosphonates separately.

9. The method of claim 8 where the pH of said aqueous system is adjusted to a pH ranging from about pH 2 to about pH 3.5 to suppress ionization of said polyacrylic acids.

10. The method of claim 8 where said non-polar adsorbent is selected from the group consisting of octadecylsilane or octylsilane bonded to silica gel and a rigid, macroreticular styrene-divinylbenzene copolymer.

11. The method of claim 8 where said displacement fluid is selected from the group consisting of methanol and an aqueous solution of sodium hydroxide.

12. The method of claim 8 where said polyacrylic acids are water soluble polymers selected from the group consisting of homopolymers of polyacrylic acid, polymethacrylic acid, and polymaleic acid, copolymers formed from at least 50 weight percent of acrylic acid, methacrylic acid, or maleic acid and less than 50 weight percent of a different copolymerizable monomer, and mixtures of said homopolymers and copolymers.

* * * * *